United States Patent [19]

Hilleman et al.

[11] 4,017,601
[45] Apr. 12, 1977

[54] HEPATITIS A ANTIGEN

[75] Inventors: Maurice R. Hilleman, Lafayette Hill; William J. Miller, North Wales; Philip J. Provost, Harleysville, all of Pa.

[73] Assignee: Merck & Co., Inc., Rahway, N.J.

[22] Filed: Oct. 16, 1975

[21] Appl. No.: 623,184

[52] U.S. Cl. .................................................. 424/89
[51] Int. Cl.² ......................................... A61K 39/12
[58] Field of Search ..................................... 424/89

[56] References Cited
OTHER PUBLICATIONS

Feinstone et al., J. of Virology vol. 13, No. 6 (1974) pp. 1412–1414.

Feinstone et al., Science, vol. 182 (Sept. 1973) pp. 1026–1028.

*Primary Examiner*—Sam Rosen
*Attorney, Agent, or Firm*—Donald J. Perrella; J. Jerome Behan

[57] ABSTRACT

Hepatitis A antigen obtained from the stools of patients infected with hepatitis A (infectious hepatitis) virus has been found to be usable in fast, simple assays for hepatitis A antibody and thus usable in diagnosis of hepatitis A disease, and for the preparation of hepatitis A vaccine.

8 Claims, No Drawings

HEPATITIS A ANTIGEN

BACKGROUND OF THE INVENTION

This invention relates to hepatitis A (infectious hepatitis) antigen and to a method for its preparation, to its use in an assay for hepatitis A, and for the preparation of hepatitis A vaccine.

Hepatitis A is a liver disease which, while not commonly fatal, can involve many weeks of debilitating illness. It is usually spread by direct contact with an infected individual or by contaminated drinking water or food. Conventional virus propagation methods have not been successful in growing hepatitis A virus. A recent invention of Drs. P. J. Provost, O. L. Ittensohn and M. R. Hilleman, described in copending U.S. Pat. Application Ser. No. 530,623, filed Dec. 9, 1974 is based on the discovery that hepatitis A virus can be obtained from the liver of infected non-human primates, e.g., marmosets. Because such non-human primates are not always available in required numbers an alternate method of obtaining hepatitis A antigen is desired.

It is, accordingly, an object of the present invention to provide a practical method for obtaining hepatitis A antigen which does not involve non-human primates. Another object is to provide hepatitis A antigen for use in an assay for hepatitis A. A further object is to provide a vaccine for hepatitis A. These and other objects of the present invention will be apparent from the following description.

SUMMARY OF THE INVENTION

Hepatitis A (infectious hepatitis) antigen is obtained from the stools of patients in the acute phase of hepatitis A disease. The stools are extracted in an aqueous medium and the extracts are centrifuged. Supernates having hepatitis A antigen titer of 1:4 or greater are usable as hepatitis A antigen in serological testing for hepatitis A antibody and for the preparation of a vaccine for hepatitis A disease.

DETAILED DESCRIPTION

It has now been found that hepatitis A antigen usable in an immune adherence hemagglutination assay and for the preparation of hepatitis A vaccine is obtained from the stools of patients in the acute phase of hepatitis A disease. According to the present invention the stools are homogenized mechanically in an aqueous medium such as a physiological salt solution, e.g. saline or phosphate buffered saline (PBS). The homogenate is centrifuged to separate solids and the supernate is assayed for hepatitis A content according to the method described in the copending patent application of William J. Miller and William J. McAleer filed Dec. 9, 1974 as Ser. No. 531,020. Extracts having antigen titers of 1:4 or greater are usable as hepatitis A antigen in the foregoing assay.

The antigen extracts can be further purified by extraction with ether at lowered temperatures with recovery of the aqueous layer. The antigen can further be heated to reduce non-specific activity of the antigen preparation.

Anitgen preparations obtained as described above, with or without ether and heat treatments, have been found to have hepatitis A antigen activity because they give positive immune adherence reactions with human sera known to contain hepatitis A antibody, and negative immune adherence reactions with human sera known to be devoid of hepatitis A antibody.

The antigen extract can also be used in the preparation of immunizing antigen, i.e., vaccine. For this purpose the stools are extracted and centrifuged as described above and the extracts having immune adherence hepatitis A antigen titer of 1:4 or greater are treated with ultrasound. The sonicated extract is centrifuged. Sediment is recovered with the aid of ultrasound and resuspended in PBS. The suspension is filtered and the filtrate applied to a cesium chloride gradient having a density range of from about 1.1 to about 1.4 grams/$cm^3$ and centrifuged.

Fractions containing viral antigen (with densities in the region of from about 1.32 to about 1.36 g/$cm^3$) are collected and dialyzed against distilled water. The antigen preparation is then extracted with an equal volume of ethyl ether at about 4° C. for from about 10 to about 30 hours. The aqueous phase is recovered, acidified to a pH of from about 2 to about 4 and allowed to stand at ambient temperature for a period of from about 1 hour to about 5 hours. The pH is then re-adjusted to approximately 7.0. The resulting antigen is then heated to from about 50 to about 65° C. for from about 0.5 to about 2 hours. The antigen preparation is clarified by centrifugation at about 2500 rpm for about 15 minutes. The supernate is reacted with 1:4000 formalin at about 37° C for about 72 hours. The excess formaldehyde is neutralized with sodium bisulfite. The resulting preparation consists of the immunizing antigen (vaccine).

The disclosure of the above-mentioned copending patent application Ser. No. 531,020 filed Dec. 9, 1974 is hereby incorporated by reference.

The following examples illustrate the present invention without, however, limiting the same thereto. All temperatures are expressed in degrees Celsius unless otherwise indicated.

EXAMPLE 1

One gram of feces collected from a patient on the day that clinical symptoms of hepatitis A are first manifested is homogenized in a 10 ml Ten Broeck tissue homogenizer in 4 ml of physiological saline. The slurry is clarified in a 5 ml SW65 tube at 10,000 rpm for 30 minutes and the pellet is discarded. The 3.5 ml extract is tested for the presence of hepatitis A antigen by the Immune Adherence assay described in copending application Ser. No. 531,020, and is found to have a hepatitis A antigen level of 1:8. The extract is confirmed for the presence of antigen by its location in CsCl at a density of 1.34, its reversal in the reverse passive hemagglutination assay by convalescent marmoset serum and by immune electron microscopy. One gram of the feces yields 16 ml of test solution antigen at the immune adherence use-level concentration which is sufficient antigen to perform 600 single well assays. A 100 g fecal sample from this patient supplies sufficient antigen to perform 60,000 single well hepatitis A assays.

EXAMPLE 2

Human stools are collected within the period of 7 days before to 7 days after clinical onset of illness in a group of hepatitis A patients. The stools are extracted by mechanical means (Ten Broeck homogenizer or Sorvall omni-mixer) to yield 20% (w/w) homogenates in phosphate-buffered saline. The homogenate is centrifuged at 10,000 rpm for 30 minutes in a Beckman type 30 angle head rotor. The supernatants are retained and assayed for hepatitis A antigen content by the immune adherence (IA) assay. Extracts giving antigen titers of 1:4 or greater are usable as hepatitis A antigen. About 1 in 5 to 1 in 10 stools examined by the above criteria yield usable antigen extracts. A part of the antigen preparation is further processed by overnight extraction with an equal volume of ether at 0° C with recovery of the aqueous layer. Another part of the antigen is heated at 56° C for 1 hour. Some of the antigen extracted with ether is also subjected to this heat treatment. These processes help to reduce non-specific activity of the antigen preparations. Antigen preparations as above, both with and without ether and heat treatment, have been found to have specific hepatitis A antigen activity, because they give positive IA reactions with human sera known to contain hepatitis A antibody, and negative IA reactions with human sera known to be devoid of hepatitis A antibody.

EXAMPLE 3

Human stools collected within the period of 7 days before to 7 days after clinical onset of illness in hepatitis A patients are extracted and homogenized and centrifuged as described in Example 2. One hundred milliliters of pooled extracts with IA hepatitis A antigen titer of 1:4 or greater are treated with ultrasound (Model W185, Heat Systems - Ultrasonics, with Bell cup) at full power for 1 minute. The sonicated extract is centrifuged at 75,000 × g for 3 hours. Sediment is recovered with the aid of ultrasound and resuspended to 20 ml. This material is filtered through a 0.45 $\mu$ Millipore filter (pretreated with veal infusion broth) with a pre-filter. The filtrate is then applied to cesium chloride gradients (36 ml volume, density 1.1 to 1.4 $gm/cm^3$) and centrifuged in a SW27 Beckman rotor for 18 hours at 27,000 rpm.

Fractions containing viral antigen (cuts with densities in the region of 1.32 – 1.36 $gm/cm^3$) are collected and dialyzed against distilled water. The volume of the preparation of this stage is 60 ml. The antigen preparation is then extracted with an equal volume of ethyl ether at 4° C for 18 hours. The aqueous phase is recovered. The antigen preparation is next acidified to pH 3.0 for a period of 3 hours at room temperature. The pH is then re-adjusted to approximately 7.0. The resulting antigen is heated to 60° C for 1 hour. The antigen preparation is spun at 2500 rpm – 15 minutes to clarify, and the supernatant is retained. At this stage the antigen preparation is reacted with 1:4000 formalin at 37° C for 72 hours. Excess formaldehyde is neutralized with bisulphite. The resulting preparation constitutes the immunizing antigen (vaccine).

By subcutaneous injection of this material into guinea pigs and marmosets (4 × 1 ml, subcutaneous, at days 0, 13, 27 and 59) both species of animals develop hepatitis A antibody (measured by IA). The marmosets do not develop hepatitis A when subsequently challenged with a known infectious dose of hepatitis A.

What is claimed is:

1. A method of obtaining hepatitis A antigen comprising collecting a stool of a hepatitis A patient within the period of from about 7 days before to about 7 days after clinical onset of hepatitis A, forming a physiological saline homogenous extract of the stool, centrifuging the mixture, assaying the supernatant liquid for hepatitis A antigen and selecting extracts having a hepatitis A antigen titer of at least 1:4.

2. A method according to claim 1 wherein the physiological saline is phosphate buffered saline.

3. A method of preparing an immunizing antigen which comprises collecting a stool of a hepatitis A patient within the period of from about 7 days before to about 7 days after clinical onset of hepatitis A, forming a physiological saline homogeneous extract of the stool, centrifuging the mixture, assaying the supernatant liquid for hepatitis A antigen and selecting extracts having a hepatitis A antigen titer of at least 1:4, treating the selected extracts with ultrasound, centrifuging the sonicated extract to form a pellet, resuspending the pellet with ultrasound, filtering the suspension, centrifuging the filtrate in a cesium chloride density gradient, collecting fractions having densities of from about 1.32 to about 1.36 $g/cm^3$, dialyzing the fractions against distilled water, extracting the fractions with ether, acidifying the aqueous phase to from about pH 2 to about pH 4, holding at ambient temperature for from about 1 to about 5 hours, adjusting the pH to about 7.0, heating to from about 50 to about 65° C. for from about 0.5 to about 2 hours, clarifying by centrifugation and treating the supernate with formaldehyde.

4. A method according to claim 3 wherein the ether extraction takes place at about 4° C. for from about 10 to about 30 hours.

5. A method according to claim 3 wherein the fractions are extracted with an equal volume of ethyl ether.

6. A method according to claim 3 wherein the aqueous phase is acidified to pH 3.

7. A method according to claim 3 wherein the holding at ambient temperature is for 3 hours.

8. A method according to claim 3 wherein the heating is for 1 hour at 60° C.

* * * * *